United States Patent
Sasso et al.

(10) Patent No.: US 7,491,411 B2
(45) Date of Patent: Feb. 17, 2009

(54) MULTIPLE COMPARTMENT BAG ASSEMBLY FOR DIALYSIS FLUID

(75) Inventors: Giuseepe Sasso, Sondalo (IT); Theodor Sandström, Lund (SE); Lars-Fride Olsson, Lund (SE); Anders Weislander, Lund (SE)

(73) Assignee: Gambro Lundia AB (SE)

( * ) Notice: Subject to any disclaimer, the term of this patent is extended or adjusted under 35 U.S.C. 154(b) by 17 days.

(21) Appl. No.: 10/500,375

(22) PCT Filed: Feb. 4, 2003

(86) PCT No.: PCT/SE03/00183

§ 371 (c)(1),
(2), (4) Date: Jun. 2, 2005

(87) PCT Pub. No.: WO03/075982

PCT Pub. Date: Sep. 18, 2003

(65) Prior Publication Data

US 2005/0224372 A1    Oct. 13, 2005

(30) Foreign Application Priority Data

Mar. 12, 2002    (IT)    ............................ MI2002A0516

(51) Int. Cl.
*A61K 33/14*    (2006.01)
(52) U.S. Cl. .................................................... 424/663
(58) Field of Classification Search ................ 424/680, 424/681, 715, 663
See application file for complete search history.

(56) References Cited

U.S. PATENT DOCUMENTS

| 4,630,727 | A | | 12/1986 | Feriani et al. |
| 5,200,200 | A | * | 4/1993 | Veech ........................ 424/663 |
| 5,211,643 | A | | 5/1993 | Reinhardt et al. |
| 5,383,324 | A | * | 1/1995 | Segers et al. .................. 53/425 |
| 6,309,673 | B1 | | 10/2001 | Duponchelle et al. |

FOREIGN PATENT DOCUMENTS

JP    6105905    4/1994

* cited by examiner

*Primary Examiner*—Johann R Richter
*Assistant Examiner*—Ali Soroush
(74) *Attorney, Agent, or Firm*—Finnegan, Henderson, Farabow, Garrett & Dunner L.L.P.

(57) ABSTRACT

The invention concerns a multiple compartment flexible bag assembly including a first predetermined volume of an aqueous sodium bicarbonate component solution contained in at least one of the multiple compartments and a second predetermined volume of an aqueous acid component solution contained in at least another of the multiple compartments, the component solutions being intended to be mixed together to obtain a peritoneal dialysis, hemodialysis or replacement fluid, characterized in that the aqueous acid component solution comprises an amount of dissolved carbon dioxide. The partial pressure value of carbon dioxide exhibited the aqueous acid component solution is preferably matched with the partial pressure value of carbon dioxide determined for the aqueous sodium bicarbonate component solution.

9 Claims, 6 Drawing Sheets

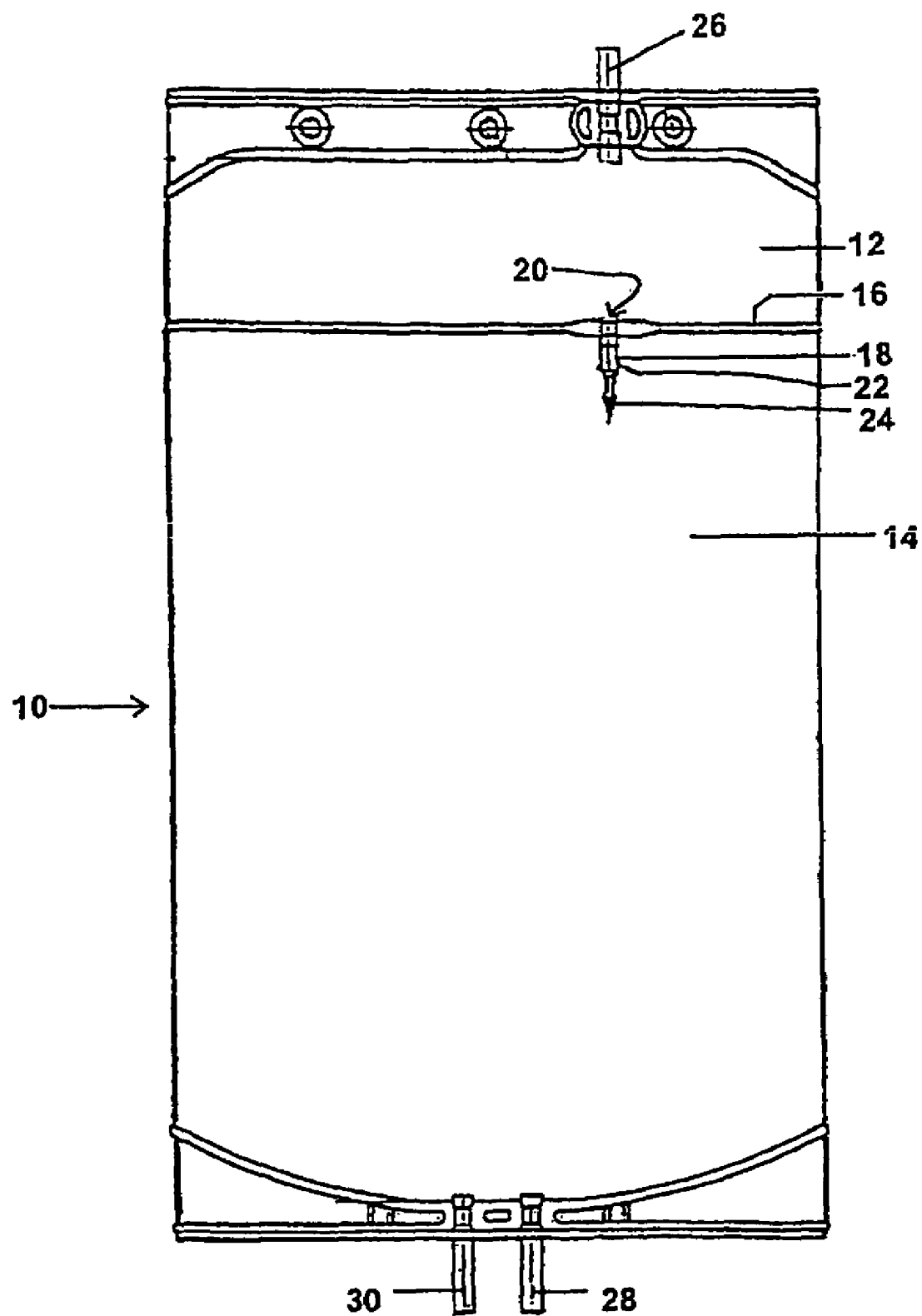
- Figure 1 -

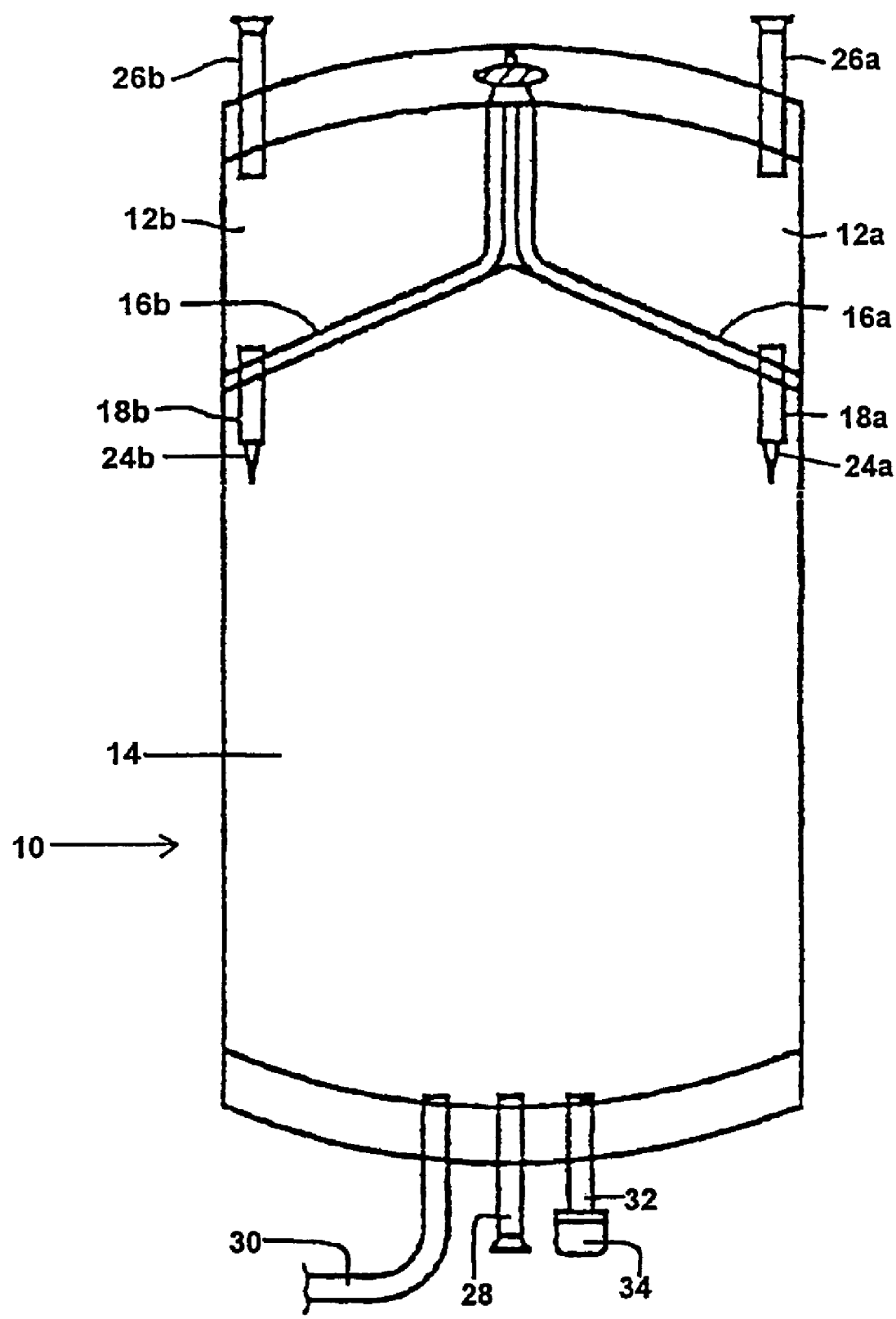
- Figure 2 -

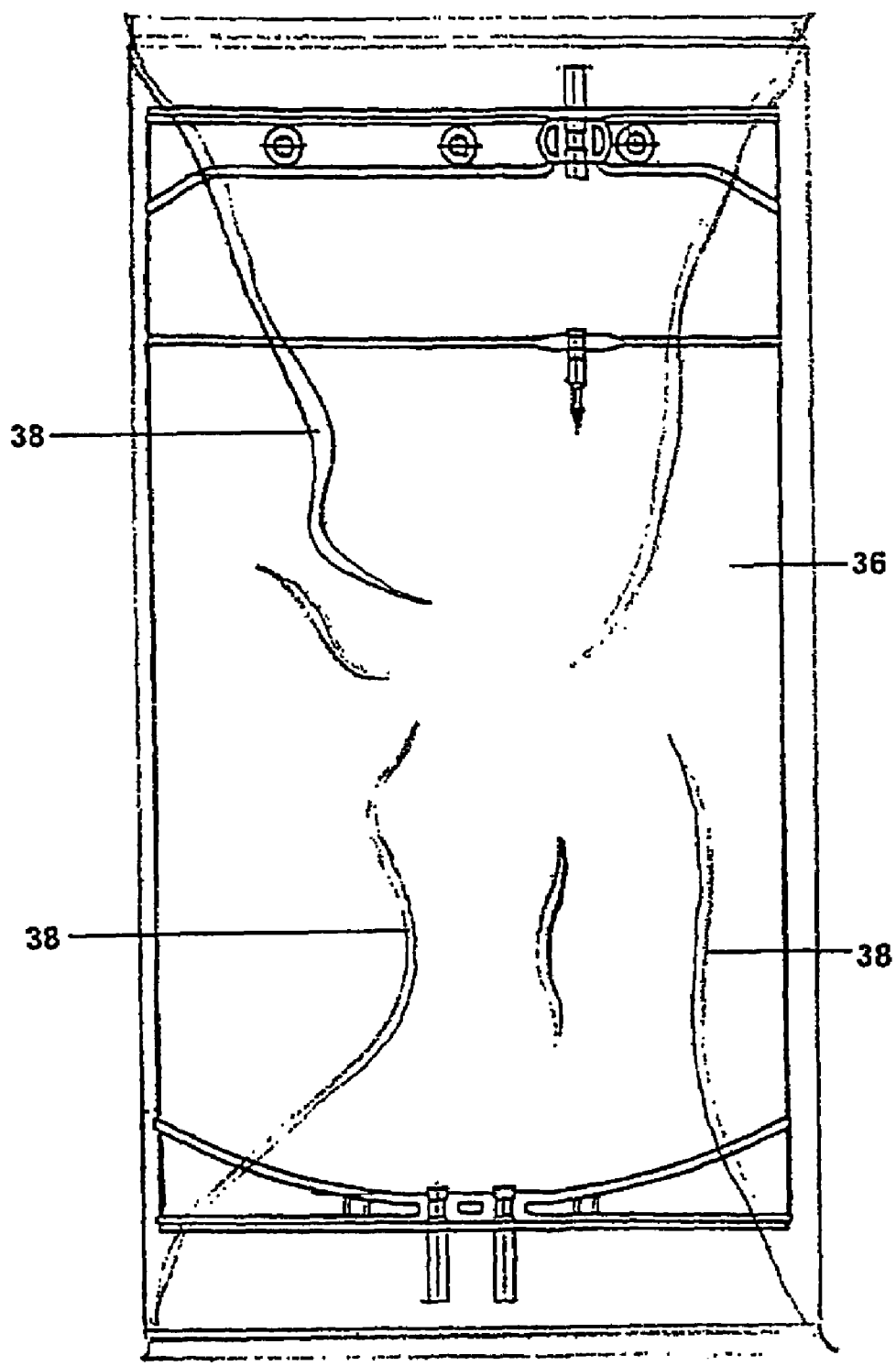
- Figure 3 -

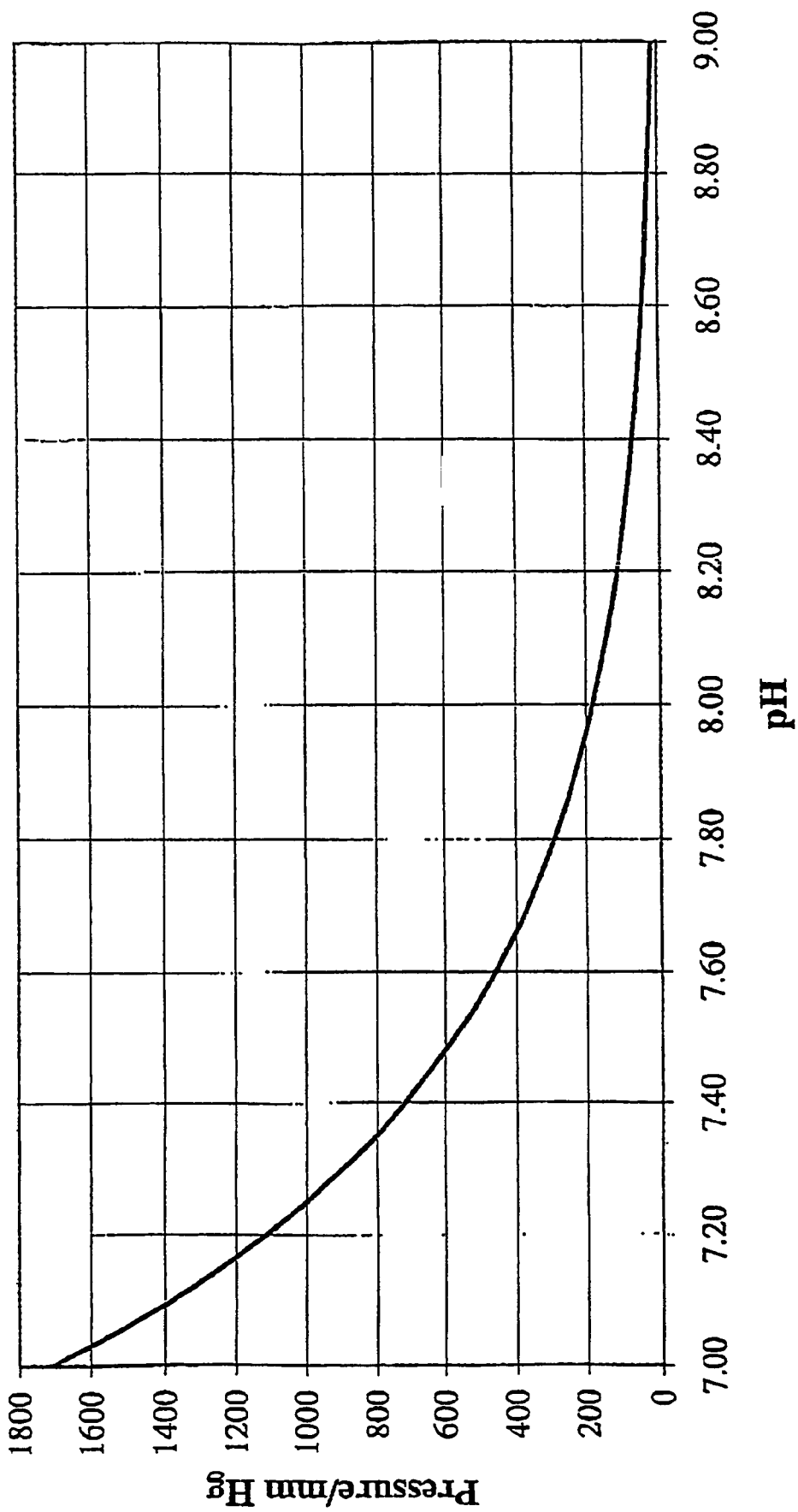
- Figure 4 -

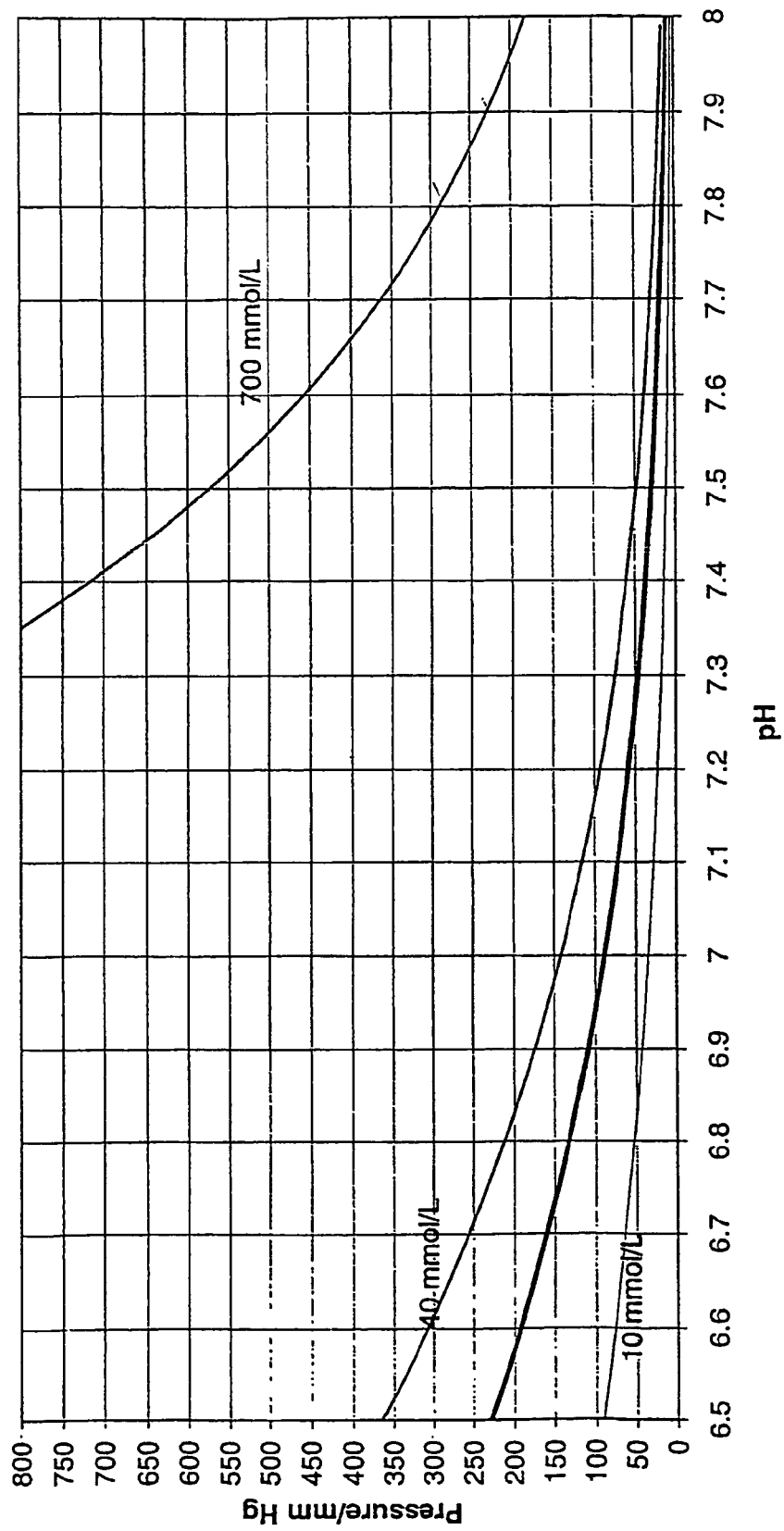
- Figure 5 -

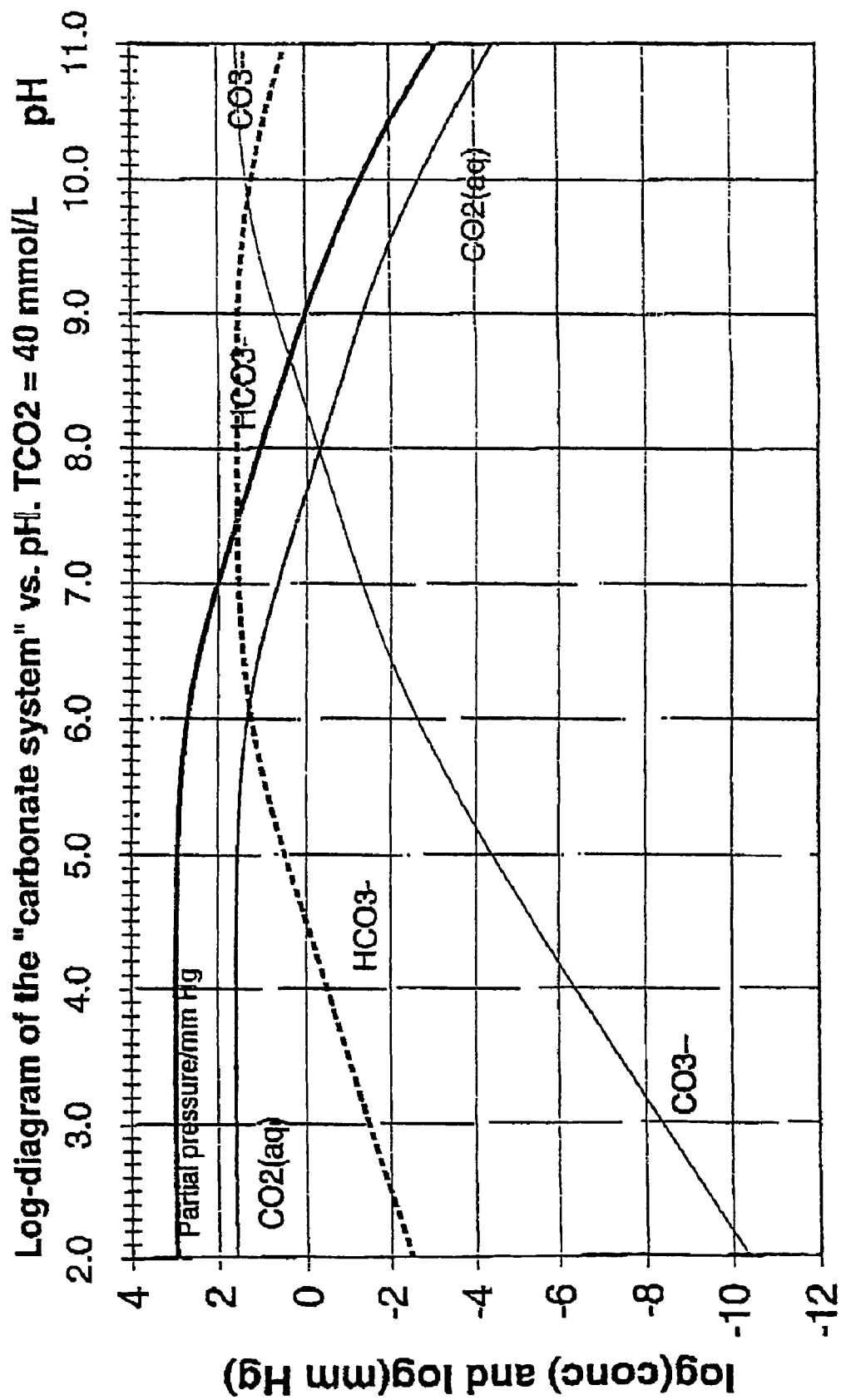
- Figure 6 -

MULTIPLE COMPARTMENT BAG ASSEMBLY FOR DIALYSIS FLUID

This invention relates to peritoneal dialysis, hemodialysis and replacement fluids. More particularly, the invention relates to a dialysis or replacement fluid separated into two or more component solutions intended for admixture preliminary to use. Admixture of the component solutions provides the final dialysis or replacement fluid.

BACKGROUND OF THE INVENTION

With the advent of bicarbonate, in general sodium bicarbonate, being the preferred buffer and indeed natural buffer as compared to acetates or lactates, dialysis and replacement fluids preferably comprise bicarbonate. Dialysis and replacement fluids comprising bicarbonate anions in general need to be provided in the form of at least two separate component solutions, one comprising essentially only the bicarbonate component and the other comprising the so-called minor electrolytes including $Ca^{++}$, $Mg^{++}$ and $K^+$ cations, and $Na^+$. In some cases, a $Na^+$-content, additional to that provided by $NaHCO_3$, may conveniently be provided together with the bicarbonate component.

The need for separation of the bicarbonate component from other components which may comprise $Ca^{++}$ and $Mg^{++}$ cations is that the required amounts of these cations, in particular $Ca^{++}$, cannot be stored together with bicarbonate for any appreciable period of time without precipitation of $Ca^{++}$ and $Mg^{++}$ carbonates. However, if the bicarbonate and $Ca^{++}$ and $Mg^{++}$ component solutions are mixed together shortly before use of the mixture as a dialysis or replacement fluid, precipitation does not occur within a time which is adequate for the mixture to be employed for its intended purpose.

One of the difficulties encountered with bicarbonate solutions i.e. in this case the bicarbonate component solution, is that such solutions are inclined to lose $CO_2$ and form carbonates, which leads to an increased pH. There are suggestions, such as provided in U.S. Pat. No. 5,211,643, that it is of importance that the pH of bicarbonate solutions should be below 7.6 if formation of calcium carbonate seeds is to be avoided when mixing of the bicarbonate solution and $Ca^{++}$-containing solution takes place, which in turn encourages further $CaCO_3$ precipitation. On the other hand, there are alternative suggestions, as represented by PCT/US00/20486 (WO 01/17534 A1) that a low pH of less than 7.6 is not critical and indeed a pH of 8.6 to 10 is indicated to be an acceptable pH range for the bicarbonate solution. In this PCT publication, it is furthermore indicated that the need, for a gas-impermeable over-wrap limiting migration or escape of $CO_2$ from the bicarbonate solution can be dispensed with. In other words, no harm is seen in allowing $CO_2$ to escape from the bicarbonate solution and for the attendant pH to increase to a value of from 8.6 up to even 10, suggesting a higher concentration of $CO_3^{--}$ ions.

The present invention is concerned with advantageous alternatives to both of the approaches discussed above. Thus, in the case of U.S. Pat. No. 5,211,643, the need for the bicarbonate solution to be possessed of a pH below 7.6 is critical to the invention there described. Products involving sodium bicarbonate solutions having a pH in excess of 7.6, for example 7.8 or even up to 8.8, however, have not demonstrated difficulties arising from calcium carbonate precipitation when mixed with $Ca^{++}$-containing solutions, provided that the mixtures are employed for their intended purpose within a reasonable period of time, such as within 24 hours from the time that the component solutions are mixed. On the other hand, it is known that bicarbonate-containing solutions contained in flexible plastic material bags are inclined to lose $CO_2$ and for the pH of the solution to thereby reach higher pH values. More particularly, it is of importance that the final mixture of the alkaline bicarbonate solution with the $Ca^{++}$-containing solution which is generally an acid solution, usually comprising both $Ca^{++}$ and $Mg^{++}$ cations, be within a physiologically acceptable pH range of about 7.2 to 7.3. It is accordingly of importance to gain proper control over the extent of $CO_2$ migration from bicarbonate solutions. One mode of gaining some control involves use of gas-impermeable over-wrap material over-wrapping flexible plastic bags each separately containing the components of the desired mixture of bicarbonate and acid solutions. One practical difficulty with this procedure is that the over-wrap material, also in the form of a flexible bag, is normally evacuated of air so that the over-wrap material seats over the surfaces of plastic material containing the bicarbonate and other solutions. This evacuation procedure inevitably leads to creases in the over-wrap material forming pockets into which $CO_2$ gas may escape through the plastic material container from the bicarbonate solution. Since the volume occupied by the over-wrap material is necessarily greater than the volume of the flexible bag containers containing the bicarbonate and other solutions, there is always a volume within the over-wrap material which can receive $CO_2$ gas escaping from the bicarbonate solution.

Escape of carbon dioxide from the sodium bicarbonate component solution may be limited by means of gas-impermeable over-wrap film material enclosing the flexible bag assembly. Over-wrap film materials having gas-impermeable characteristics include polypropylene-polyvinyl alcohol copolymers which however need to be employed in their over-wrap role subsequent to sterilization of the filled flexible bag assembly if the gas-impermeable characteristics thereof are to be retained.

Film materials employed for producing the multi-compartment flexible bag assembly might be of PVC or non-PVC type. Such materials as are presently available are however invariably permeable to carbon dioxide gas to varying degrees. Such permeation of carbon dioxide from the sodium bicarbonate component solution leads to an increase in sodium carbonate content and hence to increased pH levels. Furthermore, loss of carbon dioxide leads to a lowering of the desired content or availability of bicarbonate ions in the final admixed composition of the sodium bicarbonate component solution and the acid component solution. The escape of carbon dioxide is thus to be avoided or controlled as best as is possible.

The present invention is more particularly directed to achieving improved control and limitation of the amounts of $CO_2$ gas which can escape from bicarbonate-containing solutions into gas-impermeable over-wrap material enclosing bicarbonate-containing and other solutions. The improved control and limitation of the amounts of $CO_2$ gas which can escape or does escape from bicarbonate-containing solutions may also provide opportunities for eliminating the need for an over-wrap. An additional associated consideration is related to influences on one another of partial pressures of $CO_2$ of different solutions to be mixed together to obtain final peritoneal dislysis, hemodialysis and replacement fluids. The invention accordingly involves evaluations of the partial pressure of $CO_2$ of bicarbonate-containing solutions and other solutions with which the bicarbonate-containing solutions are to be mixed.

SUMMARY OF THE INVENTION

The invention provides a multiple compartment flexible bag assembly including a first predetermined volume of an aqueous sodium bicarbonate component solution contained in at least one of the multiple compartments and a second predetermined volume of an aqueous acid component solution contained in at least another of the multiple compartments, characterized in that the aqueous acid component solution comprises an amount of dissolved carbon dioxide.

Particular advantages of comprising an amount of carbon dioxide in the aqueous acid component solution include the fact that firstly an amount of carbon dioxide is available in this aqueous acid component solution so that, upon mixing of the bicarbonate component solution with the acid component solution, the bicarbonate solution is exposed to an environment of a $CO_2$-containing solution rather than a $CO_2$-free solution, and secondly that such amount of carbon dioxide which migrates across the packaging material from the acid component solution into a gas-impermeable over-wrap flexible bag will limit by a corresponding amount the amount of carbon dioxide which can migrate from the sodium bicarbonate component solution into said over-wrap flexible bag. On the other hand, embodiments of the multiple compartment flexible bag assembly of the invention which do not comprise a gas-impermeable over-wrap flexible bag may share the characteristic of the invention in that such embodiments may similarly avoid that bicarbonate solutions become exposed to a $CO_2$-free environment upon mixing with the acid component solution.

The amount of dissolved carbon dioxide in the aqueous acid component solution may be that amount which is dissolved in the acid component solution following on bubbling and distributing $CO_2$ gas into the bottom of a tank containing the aqueous acid component solution. Preferably, the acid component solution is maintained at a temperature of about 25° C. under atmospheric conditions during this procedure.

The amount of carbon dioxide dissolved in the aqueous acid component solution is most preferably that amount which leads to a partial pressure value for $CO_2$ ($pCO_2$) in the aqueous acid component solution which approximates or equates with the $pCO_2$ value in the bicarbonate component solution. Thus, for example, if the total $CO_2$, $HCO_3^-$, and $CO_3^{--}$ content (hereinafter $TCO_2$) of the bicarbonate solution is about 700 mmol/l and the bicarbonate component solution is to be provided in the preferable pH range of 7.8 to 8.0, the $pCO_2$ value of this solution is between about 220 and 290 mmHg at a temperature of about 20-25° C. and pressure of about 760 mm Hg. This means that from about 8 mmol/l to about 11 mmol/l of $CO_2$ should most preferably be dissolved in the aqueous acid component solution. Further more detailed explanations are provided below, with reference to an exemplary graphical representation, showing inter-relationships between $pCO_2$, pH, log [$CO_2$aq], log [$HCO_3^-$] and log [$CO_3^{--}$].

In accordance with the invention, it has furthermore been determined that, for hemodialysis and replacement solutions prepared by mixing of the bicarbonate component solution and the acid component solution, in order to achieve the desired final $HCO_3^-$ concentration of 30 to 40 mmol/l, preferably 36 mmol/l and at the same time also to achieve the preferred substantial matching of the $pCO_2$ values for the bicarbonate and acid component solutions, the pH of the bicarbonate component solution should preferably be increased by the addition of an alkaline-acting substance other than $NaHCO_3$ alone. The alkaline acting substance is most preferably $Na_2CO_3$ since $CO_3^{--}$ is one of the anion entrants comprised in the above-mentioned "$TCO_2$" total. However, the alkaline-acting substance may for example be NaOH, and/or a small amount of KOH replacing such amount of $K^+$ as may be required which is generally made available in the acid component solution. In this fashion, it is possible to establish specific predetermined $pCO_2$ values in bicarbonate-containing solutions, which values may be selected dependently of available flexible bag materials and the nature of the acid component solution or other solutions with which the bicarbonate component solution is to be mixed.

As will be more apparent from further disclosure below, the increase of the pH of the acid component solution caused by mixing with the alkaline bicarbonate component solution leads dissolved $CO_2$ to convert to carbonic acid or rather $H^+$ and $HCO_3^-$ ions, the $H^+$ or protons then being available to either convert $CO_3^{--}$ ions to $HCO_3^-$ ions or lower the pH of the mixed component solution. Any such increase in content of $HCO_3^-$ ions of course needs to be taken into account in the process of securing the correct and desirable concentration of $HCO_3^-$ ions in the final mixed component solution.

Formulations of acid component solutions of the invention for the preparation of hemodialysis (and replacement) (HD) fluids and peritoneal dialysis (PD) fluids are as follows:

|  | HD | PD |  |
|---|---|---|---|
| Sodium | 0-4000 | 0-400 | mmol/l |
| Potassium | 0-1000 | 0-5 | mmol/l |
| Calcium | 0-50 | 0-17.5 | mmol/l |
| Magnesium | 0-30 | 0-7.5 | mmol/l |
| Chloride | 0-5500 | 0-500 | mmol/l |
| Glucose | 0-2000 | 0-3000 | mmol/l |
| Acid | 0-100 | 0-100 | mmol/l |
| Dissolved $CO_2$ | 0.5-30 | 0.5-30 | mmol/l |
| pH | 2-5 | 2-5 |  |
| $pCO_2$ | 10-675 | 10-760 | mmHg |
| Water |  |  |  |

Preferably, the amount of dissolved $CO_2$ in the above solutions is within the range of 5 to 15 mmol/l leading to a $pCO_2$ value within the range of 110 to 350 mmHg at a pH of 2 to 4.3.

Exemplary acids which may be employed in the acid component solution include hydrochloric acid, acetic acid, lactic acid and of course the carbonic acid formed by the $CO_2$ dissolved in the aqueous medium when the pH of the solution is increased. Preferably, the amount of the acid (excluding carbonic acid) in the acid component solution is from 1-10 mmol/l for a dilute form and from 40-100 mmol/l for a concentrated form. Formulations of the acid component solution may furthermore comprise additional substances such as a citrate, fumarate, malate or succinate, either in the form of an acid or a salt thereof.

EXAMPLES

More specific Examples of formulations of acid component solutions of the invention for the preparation of HD fluids are set forth below:

Example 1

Dilute Form HD

| | |
|---|---|
| Calcium chloride.$2H_2O$ | 0.271 g (1.84 mmol/l) |
| Sodium chloride | 6.450 g (110 mmol/l) |
| Lactic acid | 0.284 g (3.16 mmol/l) |
| Magnesium chloride.$6H_2O$ | 0.108 g (0.53 mmol/l) |
| Dissolved $CO_2$ | 5-30 mmol/l |
| pH | 3.1 |
| $pCO_2$ | 150-750 mmHg |
| Water to volume | 1000 ml |

Example 2

Concentrated Form HD, Including Glucose

| | |
|---|---|
| Calcium chloride.$2H_2O$ | 5.145 g (34.8 mmol/l) |
| Magnesium chloride.$6H_2O$ | 2.033 g (10 mmol/l) |
| Glucose anhydrous | 22.00 g (22 mmol/l) |
| Lactic acid | 5.40 g (60 mmol/l) |
| Dissolved $CO_2$ | 5-30 mmol/l |
| pH | 2.3 |
| $pCO_2$ | 150-750 mmHg |
| Water to volume | 1000 ml |

Preferably, as already mentioned above, the amount of dissolved $CO_2$ in the above solutions is within the range of 5 to 15 mmol/l leading to a $pCO_2$ value within the range of 110 to 350 mmHg.

A more specific Example of a formulation of an acid component solutions of the invention suitable for the preparation of PD fluids is set forth below:

Example 3

PD Form

| | |
|---|---|
| Sodium chloride | 5.30 g (91 mmol/l) |
| Calcium chloride.$2H_2O$ | 4.77 g (32.2 mmol/l) |
| Magnesium chloride.$6H_2O$ | 1.62 g (8.0 mmol/l) |
| Glucose anhydrous | 500 g (2780 mmol/l) |
| Acid (HCl) | 0.2-0.4 mmol/l |
| Dissolved $CO_2$ | 5-30 mmol/l |
| pH | 3.2 |
| $pCO_2$ | 110-675 mmHg |
| Water to volume | 1000 ml |

As mentioned, the partial pressure of $CO_2$ exhibited by the aqueous acid component solution most preferably substantially matches that of the aqueous bicarbonate component solution. The invention accordingly also provides a process for preparing an aqueous acid component solution, which may be of the particular formulations described above, which comprises the steps of determining the carbon dioxide partial pressure value exhibited by an aqueous bicarbonate component solution, preparing the aqueous acid component solution, and introducing carbon dioxide into the prepared aqueous acid component solution to obtain an aqueous acid component solution which exhibits a carbon dioxide partial pressure value which substantially matches said carbon dioxide partial pressure value determined for said aqueous bicarbonate component solution. The dissolved carbon dioxide thus provides a source of protons contributing to a lowering of the pH upon admixture of a sodium bicarbonate component solution with the acid aqueous acid component solution. The pH of the sodium bicarbonate component solution may be as high as about 9.5, but is preferably less than about 8.5 at the time that admixture thereof with the acid component solution takes place. The pH of the acid component solution, may be between about 1.5 and 5, but in compositions of acid component solutions comprising glucose, the pH should most preferably be between about 3.0 and 3.4, preferably about 3.2, during sterilization processes.

A further major advantage of including carbon dioxide in the acid component solution is that the weak acid properties of carbonic acid (formed by dissolved carbon dioxide when increasing pH) enables a higher pH value to be provided in the acid component solution as compared to employing only a relatively strong acid, such as lactic acid or hydrochloric acid, for purposes of providing a source of protons depressing carbonate content by conversion to bicarbonate and lowering the pH of the sodium bicarbonate component solution when this is admixed with the acid component solution. The inclusion of carbon dioxide in the acid component solution is of particular advantage where the acid component solution also comprises amounts of glucose, such as described above, since glucose degradation products are formed during autoclaving or other sterilization processes not only at high pH but also when the pH is too low (below about 3.2). The carbon dioxide dissolved in the acid component solution provides availability of a proportion of protons required for lowering the pH of the admixed solutions while at the same time contributing to avoiding an unacceptably low pH for glucose-containing acid component solutions during sterilization processes.

The sodium bicarbonate component solution, in a fashion similar to the acid component solution may optionally also comprise dissolved carbon dioxide. Exemplary sodium bicarbonate component solutions comprise from about 10 mmol/l to 1100 mmol/l sodium bicarbonate.

Thus, for example, a sodium bicarbonate component solution suitable for use as a component of a renal intensive care substitution fluid may comprise 58.8 g/l or 700 mmol/l of sodium bicarbonate. This type of solution may initially be comprised in a tank and carbon dioxide bubbled and distributed into the bottom of the tank so that the solution becomes essentially saturated with carbon dioxide. The temperature of the solution during the time that carbon dioxide is introduced is preferably about 25° C., at the prevailing atmospheric pressure, as in the case of the acid component solution. The pH of the bicarbonate solution may be lowered to a pH of about 7.3 or even as low as 6.0 if the bicarbonate concentration is lowered, as will be apparent from the following description with reference to the accompanying drawings.

A first predetermined volume of the bicarbonate component solution is introduced into one of the compartments of the multiple compartment flexible bag assembly and a second predetermined volume of other component solutions is introduced into other of the separate compartments and the filled assembly is then subjected to heat sterilization, preferably steam-sterilization at about 120° C. $CO_2$ gas is caused to escape from the bicarbonate component solution so that the pH of this solution advantageously reaches a value of at least 6.8. Preferably, however, for stability and storage reasons, the pH of the bicarbonate component solution is allowed to rise to a pH value of between about 7.8.and 8.0 because at elevated pH values the $pCO_2$ values in the bicarbonate component solution are significantly lower than at lower pH values. Thus, the tendency for $CO_2$ to migrate across the walls of the packaging material is reduced and the stability of the bicarbonate solution is increased substantially.

Exemplary formulations of sodium bicarbonate component solutions suitable for the preparation of HD fluids, after steam-sterilization, are as follows:

Example 4

Concentrated Form HD

| | |
|---|---|
| Sodium bicarbonate | 58.8 g (700 mmol/l) |
| Water to volume | 1000 ml |
| Min. conc. $CO_2$ | 11 mmol/l |
| Max. conc. with added $CO_2$ | 30 mmol/l |
| pH (at min. $CO_2$) | 7.8 |
| pH (with added $CO_2$) | 7.4 |
| $pCO_2$ (at min. $CO_2$) | 300 mmHg |
| $pCO_2$ (at max. $CO_2$) | 760 mmHg |

Example 5

Dilute Form HD, Including $K^+$

| | |
|---|---|
| Sodium chloride | 6.450 g (110 mmol/l) |
| Sodium bicarbonate | 3.090 g (36.8 mmol/l) |
| Potassium chloride | 0.157 g or 0.314 g (2 mmol/l or 4 mmol/l) |
| Water to volume | 1000 ml |
| Min. conc. $CO_2$ | 0.5 mmol/l |
| Max. conc. (with added $CO_2$) | 33 mmol/l |
| pH (at min. $CO_2$) | 7.9 |
| pH (with added $CO_2$) | 6.2 |
| $pCO_2$ (at min. $CO_2$) | 11 mmHg |
| $pCO_2$ (at max. $CO_2$) | 760 mmHg |

Example 6

Concentrated Form HD

| | |
|---|---|
| Sodium bicarbonate | 42 g (500 mmol/l) |
| Sodium carbonate | 44 g (415 mmol/l) |
| Water to volume | 1000 ml |
| $CO_2$ conc. | 0.28 mmol/l |
| pH | 9.3 |
| $pCO_2$ | 11 mmHg |

An exemplary formulation of a sodium bicarbonate component solution suitable for preparation of PD fluids is set forth below:

Example 7

PD Form

| | |
|---|---|
| Sodium chloride | 7.77 g (134 mmol/l) |
| Sodium bicarbonate | 0.882 g (10.5 mmol/l) |
| Sodium lactate | 3.54 g (31.6 mmol/l) |
| $CO_2$ conc. | 4 mmol/l |
| Water to volume | 1000 ml |
| pH | 6.5 |
| $pCO_2$ | 90 mmHg |

A first predetermined volume of the above Example 4 sodium bicarbonate component concentrated form solution is to be related to, i.e. admixed, with a second predetermined volume of the above Example 1 of acid component dilute form solution to obtain a final HD (or replacement) fluid. The total unit volume of the final HD fluid is conveniently selected to be 5 l. Thus, a first predetermined volume of said sodium bicarbonate solution would be 0.25 l to be admixed with a second predetermined volume of 4.75 l of said first formulation of acid component solution to provide 5 l of final HD or replacement fluid having the following composition:

| | |
|---|---|
| Calcium | 1.75 mmol/l |
| Magnesium | 0.5 mmol/l |
| Sodium | 140 mmol/l |
| Chloride | 109 mmol/l |
| Lactate | 3.0 mmol/l |
| Bicarbonate | 32.0 mmol/l |
| pH | 7.0-7.4 |

Thus, in the above embodiment 0.25 l of the sodium bicarbonate component concentrated form solution would be contained in one compartment of a multiple compartment flexible bag assembly and 4.75 l of the acid component dilute form solution would be contained in another of the multiple compartments.

Similarly and conversely, a first predetermined volume of the above Example 5 sodium bicarbonate component dilute form solution (including potassium) is to be related to, i.e.—admixed, with a second predetermined volume of the above Example 2 acid component concentrated form solution to obtain a final HD (or replacement) fluid. The total unit volume of the final HD fluid is conveniently once again selected to be 5 l, in which case 4.75 l of said sodium bicarbonate component dilute form solution would be mixed with 0.25 l of said acid component concentrated form solution (including glucose) to obtain a final HD fluid having the following composition:

| | |
|---|---|
| Calcium | 1.75 mmol/l |
| Magnesium | 0.5 mmol/l |
| Sodium | 140 mmol/l |
| Chloride | 109 mmol/l |
| Lactate | 3.0 mmol/l |
| Bicarbonate | 32.0 mmol/l |
| Glucose | 6.1 mmol/l |

-continued

| | |
|---|---|
| Potassium | 2 or 4 mmol/l |
| pH | 7.0-7.4 |

Thus, in the above embodiment 0.25 l of the acid component solution would be contained in one compartment of the multiple compartment flexible bag assembly and 4.75 l of the bicarbonate component solution would be contained in another of the multiple compartments.

A first predetermined volume of the above Example 7 PD sodium bicarbonate component solution is to be related to, i.e. admixed, with a second predetermined volume of the formulation of the above Example 3 PD acid component solution to obtain a final PD fluid. In the case of PD fluids, the total unit volume selected is generally about 2 l. Thus, as is described in our earlier Patent Application PCT/SE98/02146, for example, the second predetermined volume of said PD acid component solution may be either 60 ml or 100 ml or 160 ml (100 ml plus 60 ml) of the PD acid component solution to be admixed with a first predetermined volume of 1900 ml of said PD sodium bicarbonate component solution, which selection of second predetermined volumes provides opportunity to obtain three different types of PD solution as follows:

| | 60 ml | 100 ml | 160 ml |
|---|---|---|---|
| Magnesium | 0.25 | 0.40 | 0.62 mM |
| Calcium | 1.0 | 1.6 | 2.5 mM |
| Sodium | 131.8 | 131.0 | 129.9 mM |
| Chloride | 92.5 | 94 | 96.2 mM |
| Bicarbonate | 10.2 | 10.0 | 9.7 mM |
| Lactate | 30.6 | 30.0 | 29.2 mM |
| pH | 7.3 | 7.3 | 7.3 |

Thus, a first predetermined volume of 1900 ml of the PD sodium bicarbonate component solution would be contained in one of the compartments of the multiple compartment flexible bag assembly, and two separate second predetermined volumes of the PD acid component solution would be contained in two separate other compartments.

A process of the invention for preparing a multi-compartment flexible bag assembly including an amount of an aqueous sodium bicarbonate component solution in at least one of the multi-compartments and an aqueous acid component solution in at least another of the multi-compartments, includes the steps of providing a multi-compartment flexible bag assembly, each compartment being dimensioned to receive a predetermined volume of a component solution, preparing the aqueous sodium bicarbonate component solution and the aqueous acid component solution, dissolving an amount of carbon dioxide in at least the aqueous acid component solution, introducing the prepared aqueous sodium bicarbonate component solution into at least one of the multi-compartments of the multi-compartment flexible bag assembly, introducing the carbon dioxide-containing aqueous acid component solution into another of the multi-compartments of the multi-compartment flexible bag assembly, and subjecting the filled multi-compartment assembly to a sterilization procedure. The sterilization procedure generally followed is steam-sterilization under pressure at 120° C., but other procedures such as heat-sterilization or γ-sterilization may be followed, dependently of such factors as the nature of the component solutions and the materials of the flexible bag assembly.

Subsequent to the sterilization procedure, where this is for example a heat or steam-sterilization procedure, the filled multi-compartment assembly is generally allowed to cool to room temperature, e.g. about 20° C. The filled multi-compartment assembly may, either before or after the sterilization procedure, dependent on the need or availability of materials, be over-wrapped with a gas-impermeable plastic material film or aluminum enclosure for purposes of retaining such amounts of carbon dioxide gas which may migrate across the walls of the flexible bag assembly from the bicarbonate and acid component solutions within the over-wrapping.

As already mentioned, additional to dissolving carbon dioxide gas in the aqueous acid component solution, it is preferable, in accordance with a process of the invention, also to dissolve carbon dioxide gas in the prepared sodium bicarbonate solution. In this way, the pH of the sodium bicarbonate solution may be lowered by the weak acid effect of carbonic acid formed by the dissolution of carbon dioxide in the aqueous medium of the sodium bicarbonate solution.

Regarding film materials employed for producing the multi-compartment flexible bag assembly, it is noted that some PVC materials may not be suited for containing solutions having a pH in excess of about 6.5. Thus, where a sodium bicarbonate solution is envisaged as one of the component solutions, as in the present invention, a specially adapted PVC able to withstand higher pH values should be employed. Exemplary of such a PVC material is one made available by Draka of Holland under the Trademark "Alka". It is understood that this PVC material comprises plasticiser or lubricant contents which are different from those of conventional PVC materials.

Dialysis or replacement fluids of the invention may comprise an amount of glucose, for example 0 mmol/l to about 250 mmol/l in the final admixed solutions. The glucose component may be comprised in the carbonated acid component solution comprising the minor electrolytes. However, it is also possible and sometimes preferable to provide a third separate glucose component solution, separate of the bicarbonate and acid component solutions, which can be of advantage in that the pH of the glucose component solution can be set to the ideal pH value for heat or steam sterilization. Thus, it is most preferable that a glucose solution be at a pH of 3.2±0.1 if the formation of glucose degradation products (GDP's) during sterilization are to be kept to a minimum. Similarly, it is preferable, although not essential at lower pH levels, to keep the glucose separate from the minor electrolytes, in particular $Ca^{++}$, during heat or steam sterilization processes.

Exemplary sodium bicarbonate-containing solutions comprised in one compartment of the multi-compartment flexible bag assembly comprise from about 600 mmol/l, to 800 mmol/l of solution. The solution most preferably comprises an amount of dissolved $CO_2$ leading to formation of carbonic acid, or another acid such as hydrochloric acid or citric acid for purposes of lowering the pH of the bicarbonate solution to a pH value somewhat less than 8, preferably less than 7.4, so that after heat sterilization, during which an amount $CO_2$ is lost, the bicarbonate solution is at a pH which does not exceed about 8 and is preferably in the range of 7.8 to 7.9. This bicarbonate component solution, when mixed with the acid component solution and optionally a separate glucose-containing component solution, should provide a final solution for use as a dialysis liquid or replacement fluid which is possessed of a pH of 7.2 to 7.4, i.e. in the physiologically acceptable range.

Additional to dissolving $CO_2$ in both the bicarbonate component solution and the acid component solution, $CO_2$ may also be dissolved in a separately prepared glucose component solution which is to be filled into a separate compartment of the multi-compartment flexible bag assembly. This dissolved $CO_2$ can also contribute to limiting the loss of $CO_2$ from the sodium bicarbonate component solution, in the same fashion as does the $CO_2$ dissolved in the acid component solution.

BRIEF DESCRIPTION OF DRAWINGS

Exemplary multi-compartment flexible bag assemblies are shown in the accompanying drawings:

FIG. 1 shows a dual-compartment flexible bag assembly;

FIG. 2 shows a triple-compartment flexible bag assembly; and

FIG. 3 shows a multi-compartment flexible bag assembly over-wrapped with a gas-impermeable over-wrap material.

The accompanying drawings also include graphical representations in which:

FIG. 4 shows the relationship, by way of example, of the influence of pH on the partial pressure of $CO_2$ ($pCO_2$) on a sodium bicarbonate, optionally including an amount of sodium carbonate and $CO_2$, but in any event providing a total "$TCO_2$"=to about 700 mmol/l, $TCO_2$ being $[HCO_3^-]+[CO_3^{--}]+[CO_2 aq]$;

FIG. 5 shows the $pCO_2$ values of various "$TCO_2$" bicarbonate solutions (optionally comprising sodium carbonate and $CO_2$) as influenced by the pH of the solution; and FIG. 6 shows the logarithmic inter-relationship of the concentrations of dissolved $CO_2$ ($CO_2$ aq), $HCO_3^-$ and $CO_3^{--}$ for a $TCO_2$ solution=40 mmol/l as influenced by pH. This figure also reflects the $pCO_2$ value for this particular $TCO_2$ solution as influenced by pH.

DETAILED DESCRIPTION OF DRAWINGS

Referring to FIG. 1 of the drawings, reference numeral 10 refers generally to a two-compartment flexible bag assembly, one compartment being referred to by reference numeral 12 and the other by reference numeral 14. One of the compartments, i.e. either the compartment 12 or the compartment 14 may contain a first predetermined volume of an aqueous sodium bicarbonate solution and the other compartment 14 or 12 may contain a second predetermined volume of an aqueous acid component solution. The compartments 12 and 14 are divided by a transverse seal 16. A communication conduit 18 is provided between the seal 16 which has an open end 20 opening into compartment 12 and a temporarily closed end 22 located in compartment 14. The temporarily closed end 22 is closed by means of a frangible pin 24 which, when manually broken opens the communication conduit 18 to enable the aqueous solution contained in the compartment 12 to be introduced into the compartment 14 and thus mixed with the aqueous solution contained in the compartment 14. Reference numerals 26 and 28 refer to filling conduits for filling the compartments 12 and 14 with the predetermined volumes of aqueous solutions. Reference numeral 30 refers to an outlet conduit for connection to a fluid line leading to HD (or substitution) monitoring equipment (not shown) or to a PD cycler (not shown) for introducing or replacing PD fluid in to the peritoneal cavity of a patient undergoing treatment.

In FIG. 2, the same reference numerals as in FIG. 1 are employed to refer to the same structural aspects of a three-compartment flexible bag assembly 10. In FIG. 2, two compartments 12a and 12b are provided to contain two different quantities of an aqueous acid component solution, e.g. 60 ml and 100 ml, as described in the disclosure above. Seals 16a and 16b, communication conduits 20a and 20b, filling conduits 26a and 26b and 28 serve the same functions as described in relation to FIG. 1. Reference numeral 32 refers to a drug delivery conduit carrying a re-seal plug 34 enabling a drug component to be introduced into the compartment 14.

FIG. 3 shows the two-compartment flexible bag assembly of FIG. 1 enclosed within a gas-impermeable over-wrap 36. The over-wrap is shown in an evacuated condition, reference numerals 38 referring to creases which form in the over-wrap material following an evacuation. The flexible bag assembly of FIG. 2 may be similarly enclosed in over-wrap 36.

Referring to FIGS. 4 and 5 inter-relationships between partial pressures of $CO_2$ and pH at various concentrations of sodium carbonate can be noted. A portion of the graphic shown for a concentration of 700 mmol/l sodium bicarbonate in FIG. 4 is included in FIG. 5.

Now, referring to FIG. 6, there is shown the logarithmic inter-relationships of concentrations of $CO_3^{--}$, $HCO_3^-$, and $CO_2$ (aq), i.e. dissolved $CO_2$, at pH values between 2 and 11. Also shown is the logarithmic inter-relationship of the $CO_2$ partial pressure to said logarithmic inter-relationships of concentrations between said pH values. When bearing in mind that the present invention provides dissolved $CO_2$ in the acid component solution and that it is preferable that the $pCO_2$ value for the acid component solution approximates that of the bicarbonate component solution, it may for example be noted from FIG. 5 that a high concentration bicarbonate component solution (700 mmol/l) at the preferred pH of 7.8 to 8 exhibits a $pCO_2$ value of between about 280 and 180 mm Hg. respectively. Accordingly, in this case the acid component solution which may be at a pH of 2 to 4 should most preferably be treated with $CO_2$ so as also to exhibit a $pCO_2$ value within or resembling this range. Similarly, if the bicarbonate component solution is for example 40 mmol/l and the pH of this solution is once again to be within the preferable pH range of 7.8 to 8, the bicarbonate component solution would exhibit a $pCO_2$ value of between about 18 and 11 mm Hg.

What is claimed is:

1. A flexible bag assembly comprising:
   at least first and second compartments;
   a first predetermined volume of an aqueous sodium bicarbonate component solution, said first predetermined volume being provided in at least one of the at least first and second compartments; and
   a second predetermined volume of an aqueous acid component solution, said second predetermined volume being provided in at least another of the at least first and second compartments, said aqueous acid component solution having an amount of dissolved carbon dioxide, the aqueous sodium bicarbonate component solution and the aqueous acid component solution being mixable together to obtain a peritoneal dialysis, hemodialysis, or replacement fluid, wherein the amount of dissolved carbon dioxide in the aqueous acid component solution is such that a partial pressure value of said carbon dioxide exhibited by said aqueous acid component solution substantially matches a partial pressure value of carbon dioxide exhibited by said aqueous sodium bicarbonate component solution.

2. A flexible bag assembly according to claim 1, wherein said aqueous acid component solution has an amount of dissolved carbon dioxide, a concentration of said dissolved carbon dioxide in the aqueous acid component solution being from 0.5 to 30 mmol/l.

3. A flexible bag assembly according to claim 2, wherein the concentration of said dissolved carbon dioxide is from 5 to 15 mmol/l.

4. A flexible bag assembly according to claim 1, wherein said aqueous acid component solution include electrolytes, glucose, acid and said dissolved carbon dioxide within the range of concentrations, pH, and $pCO_2$ values as follows:

| | |
|---|---|
| Sodium | 0 to 4000 mmol/l |
| Potassium | 0 to 1000 mmol/l |
| Calcium | 0 to 50 mmol/l |
| Magnesium | 0 to 30 mmol/l |
| Chloride | 0 to 5500 mmol/l |
| Glucose | 0 to 2000 mmol/l |
| Acid | 0 to 100 mmol/l |
| Dissolved $CO_2$ | 0.5 to 30 mmol/l |
| pH | 2 to 5 |
| $pCO_2$ | 10 to 675 mmHg. |

5. A flexible bag assembly according to claim 4, wherein the concentration of said dissolved carbon dioxide is from 5 to 15 mmol/l.

6. A flexible bag assembly according to claim 1, wherein said aqueous acid component solution includes electrolytes, glucose, acid, and said dissolved carbon dioxide within the range of concentrations, pH, and $pCO_2$ values as follows:

| | |
|---|---|
| Sodium | 0 to 400 mmol/l |
| Potassium | 0 to 5 mmol/l |
| Calcium | 0 to 17.5 mmol/l |
| Magnesium | 0 to 7.5 mmol/l |
| Chloride | 0 to 500 mmol/l |
| Glucose | 0 to 3000 mmol/l |
| Acid | 0 to 100 mmol/l |
| Dissolved $CO_2$ | 0.5 to 30 mmol/l |
| pH | 2 to 5 |
| $pCO_2$ | 10 to 760 mmHg. |
| Water | |

7. A flexible bag assembly according to claim 6, wherein the concentration of dissolved carbon dioxide is from 5 to 15 mmol/l.

8. A flexible bag assembly according to claim 1, wherein said flexible bag assembly is over-wrapped in a flexible, gas-impermeable plastic material.

9. A process for preparing an aqueous acid component solution, said aqueous acid component solution being provided in at least a first or second compartment of the flexible bag assembly of claim 1, the process comprising the steps of:
  determining a carbon dioxide partial pressure value exhibited by an aqueous bicarbonate component solution;
  preparing an aqueous acid component solution; and
  introducing carbon dioxide into the prepared aqueous acid component solution to obtain an aqueous acid component solution having a carbon dioxide partial pressure value substantially matching said carbon dioxide partial pressure value determined for said aqueous bicarbonate component solution.

* * * * *